US010076482B2

(12) United States Patent
Aubrun et al.

(10) Patent No.: US 10,076,482 B2
(45) Date of Patent: *Sep. 18, 2018

(54) SOFT SOLID OIL-IN-WATER EMULSION COMPRISING A MIXTURE OF NONIONIC SURFACTANTS, A WATER-SOLUBLE POLYSACCHARIDE AND A WAX COMPRISING AT LEAST ONE ESTER

(71) Applicant: L'OREAL, Paris (FR)

(72) Inventors: Odile Aubrun, Antony (FR); Fabrice Springinsfeld, Fresnes (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/769,235

(22) PCT Filed: Feb. 14, 2014

(86) PCT No.: PCT/EP2014/052923
§ 371 (c)(1),
(2) Date: Aug. 20, 2015

(87) PCT Pub. No.: WO2014/128058
PCT Pub. Date: Aug. 28, 2014

(65) Prior Publication Data
US 2016/0000681 A1 Jan. 7, 2016

Related U.S. Application Data

(60) Provisional application No. 61/768,926, filed on Feb. 25, 2013.

(30) Foreign Application Priority Data

Feb. 21, 2013 (FR) ..................................... 13 51476

(51) Int. Cl.
A61K 8/60 (2006.01)
A61K 8/34 (2006.01)
(Continued)

(52) U.S. Cl.
CPC ............ A61K 8/602 (2013.01); A61K 8/0229 (2013.01); A61K 8/062 (2013.01); A61K 8/26 (2013.01); A61K 8/342 (2013.01); A61K 8/37 (2013.01); A61K 8/604 (2013.01); A61K 8/732 (2013.01); A61K 8/891 (2013.01); A61K 8/922 (2013.01);
(Continued)

(58) Field of Classification Search
None
See application file for complete search history.

(56) References Cited

U.S. PATENT DOCUMENTS 5,362,482 A * 11/1994 Yoneyama ............... A61K 8/06
424/403
2003/0031643 A1* 2/2003 L'alloret .................. A61K 8/06
424/70.16
(Continued)

FOREIGN PATENT DOCUMENTS

| DE | 19962878 A1 | 6/2001 |
| DE | 102006020382 A1 | 10/2007 |
| EP | 1584330 A1 | 10/2005 |
| EP | 2095808 A1 | 9/2009 |
| EP | 2436369 A1 | 4/2012 |
| KR | 2007052486 A * | 5/2007 |
| WO | WO-01/74306 A2 | 10/2001 |
| WO | WO-2012/084522 A2 | 6/2012 |

OTHER PUBLICATIONS

"Candelilla Wax", Food and Agriculture Organization of the United Nation, Jan. 1, 2005.

Primary Examiner — Susan T Tran
(74) Attorney, Agent, or Firm — Polsinelli PC

(57) ABSTRACT

The present invention relates to a composition in the form of an oil-in-water emulsion, comprising, in a cosmetically acceptable medium: A) a continuous aqueous phase and B) an oily phase dispersed in the said aqueous phase and comprising at least one hydrocarbon-based oil; C) at least one mixture consisting of: i) at least one nonionic surfactant containing a saturated linear hydrocarbon-based chain comprising at least 16 carbon atoms, the said surfactant being other than a fatty alcohol, and ii) at least one fatty alcohol chosen from: —a pure fatty alcohol comprising more than 16 carbon atoms; —a mixture consisting exclusively of fatty alcohols containing at least 16 carbon atoms and comprising at least 50% by weight of fatty alcohol containing at least 18 atoms relative to the weight of the fatty alcohol mixture; and D) at least one wax with a melting point of greater than 45° C. comprising one or more $C_{40}$-$C_{70}$ ester compounds and not comprising any $C_{20}$-$C_{39}$ ester compounds, in an amount from 1 to 10% by weight relative to the total weight of the composition and E) at least one water-soluble polysaccharide; the said composition having a hardness measured at 32° C. and at a humidity of 40% ranging from 20 kPa to 200 kPa and preferably ranging from 25 kPa to 150 kPa. The present invention also relates to a cosmetic process for treating and/or caring for human keratin materials, characterized in that it consists in applying to the surface of the keratin material a composition as defined previously. The present invention also relates to a cosmetic process for treating human perspiration and/or perspiration-related body odor, which consists in applying to the surface of a human keratin material a composition as defined previously comprising at least one deodorant active agent and/or one antiperspirant active agent.

21 Claims, No Drawings

(51) Int. Cl.
*A61K 8/37* (2006.01)
*A61Q 15/00* (2006.01)
*A61K 8/73* (2006.01)
*A61K 8/92* (2006.01)
*A61K 8/06* (2006.01)
*A61K 8/02* (2006.01)
*A61K 8/26* (2006.01)
*A61K 8/891* (2006.01)
*A61Q 19/00* (2006.01)

(52) U.S. Cl.
CPC .............. *A61K 8/927* (2013.01); *A61Q 15/00* (2013.01); *A61K 2800/591* (2013.01); *A61Q 19/00* (2013.01)

(56) References Cited

U.S. PATENT DOCUMENTS

2005/0287104 A1* 12/2005 Aubrun-Sonneville ..................... A61K 8/0208
424/70.22
2006/0223737 A1* 10/2006 Sebillotte-Arnaud ..................... A61K 8/046
510/407

* cited by examiner

SOFT SOLID OIL-IN-WATER EMULSION COMPRISING A MIXTURE OF NONIONIC SURFACTANTS, A WATER-SOLUBLE POLYSACCHARIDE AND A WAX COMPRISING AT LEAST ONE ESTER

CROSS REFERENCE TO RELATED APPLICATIONS

This application is a National Phase filing under 35 U.S.C. § 371 of PCT/EP2014/052923 filed on Feb. 14, 2014; and this application claims priority to Application No. 1351476 filed in France on Feb. 21, 2013; and this application claims the benefit of U.S. Provisional Application No. 61/768,926 filed on Feb. 25, 2013. The entire contents of each application are hereby incorporated by reference.

The present invention relates to a composition in the form of an oil-in-water emulsion, comprising, in a cosmetically acceptable medium:

A) a continuous aqueous phase and
B) an oily phase dispersed in the said aqueous phase and comprising at least one hydrocarbon-based oil;
C) at least one mixture consisting of:
i) at least one nonionic surfactant containing a saturated linear hydrocarbon-based chain comprising at least 16 carbon atoms, the said surfactant being other than a fatty alcohol, and
ii) at least one fatty alcohol chosen from:
a pure fatty alcohol comprising more than 16 carbon atoms;
a mixture consisting exclusively of fatty alcohols containing at least 16 carbon atoms and comprising at least 50% by weight of fatty alcohol(s) containing at least 18 atoms; and
D) at least one wax with a melting point of greater than 45° C. comprising one or more $C_{40}$-$C_{70}$ ester compounds and not comprising any $C_{20}$-$C_{39}$ ester compounds, in an amount from 1 to 10% by weight relative to the total weight of the composition and
E) at least one water-soluble polysaccharide; the said composition having a hardness measured at 32° C. and at a humidity of 40% ranging from 20 kPa to 200 kPa and preferably ranging from 25 kPa to 150 kPa.

The present invention also relates to a cosmetic process for treating and/or caring for human keratin materials, characterized in that it consists in applying to the surface of the keratin material a composition as defined previously.

The present invention also relates to a cosmetic process for treating human perspiration and/or perspiration-related body odour, which consists in applying to the surface of a human keratin material a composition as defined previously comprising at least one deodorant active agent and/or one antiperspirant active agent.

In the field of cosmetic skincare products, especially deodorant and antiperspirant products, various galenical categories may be defined: aerosols, sticks, creams, gels, soft solids, roll-ons.

In the field of deodorants and antiperspirants, "soft solid" compositions constitute a new category of products that are appreciated by consumers for their efficacy and their cosmetic qualities (ease of application, soft, dry feel). They are likened to solid compositions that soften under the effect of a stress such as spreading over the surface of the skin or, for example, by extrusion through a device with a perforated wall (grille). "Soft solid" compositions, by virtue of their fondant texture, may also find increased value as care products for human keratin materials such as the skin or the lips, or as massage products, balms or pomades, or lipcare sticks. They have been described in particular in patent application WO 2012/084 522. On account of their anhydrous texture, these formulations may appear greasy, present on the skin and lacking in freshness.

In contrast, roll-ons constitute a range of fresh, fluid products which may occasionally be considered as being tacky and very slow to dry.

There is thus still a need to produce "soft solid" cosmetic skincare formulations, especially deodourant and/or antiperspirant products that are stable on storage (especially showing no creaming or leaching), combining ease of application, an immediate dry, soft, non-wetting and non-tacky feel, and which are effective in the desired application.

Patent EP 1 550 435 discloses deodourant and/or antiperspirant creams that are stable on storage, in the form of an oil-in-water emulsion containing a surfactant consisting of a mixture of alkylpolyglucoside/fatty alcohol combined with a polyurethane polyether, and which may be conditioned in a grille stick or in a tube. These formulations do not have the desired soft solid texture.

Patent application WO 2004/112 739 describes thick antiperspirant creams having viscosities ranging from 80 000 to 120 000 mPa·s (5 rpm). The compositions contain a high level of co-surfactants (glyceryl stearate), which have a tendency to produce a tacky effect after application. These formulations do not have the desired soft solid texture.

Henkel patent EP 1 239 822 describes antiperspirant creams containing water, water-insoluble particulate polysaccharides, at least one antiperspirant active agent and at least one wax comprising an ester of a $C_{16\text{-}60}$ alcohol and of a $C_8$-$C_{36}$ carboxylic acid. They are in the form of a thick cream with a viscosity of greater than 50 000 mPa·s (Heliopath, 4 rpm, 21° C.). These formulations do not have the desired soft solid texture and the presence of high concentrations of particulate starch may lead to white marks on the skin and clothing.

We know in the application EP2436369 oil-in-water emulsions based on a mixture of waxes comprising a) at least one paraffin wax and/or at least one polyethylene wax, b) at least one monocrystalline wax and c) at least one animal/plant wax containing an ester of a $C_{20}$-$C_{32}$ fatty acid cide and a $C_{28}$-$C_{34}$ fatty alcohol in the aim of obtaining creams having a good stability on storage, producing onto the skin an elastic sensation and good resilience and stickyness. The Candelilla was associated to the waxy components a) and b) do not allow, according to this document, to obtain a sufficiently stable cream. This document does not suggest to manufacture compositions having the expected soft-solid texture.

We know in the application DE19962878 oil-in-water emulsions with esters waxes of $C_{18}$-$C_{60}$ fatty alcohol and $C_8$-$C_{36}$ monocarboxylic acid and watersoluble polysaccharides. In particular, examples 29 and 30 are oil-in-water emulsions with hydrocarbon oils, non-ionic surfactants having a linear and saturated hydrocarbon chain comprising at least 16 carbon atoms (ceteareth-20, glycerylstearate), a $C_{20}$-$C_{40}$ ester wax: Kesterwachs $C_{20}$-$C_{40}$ Alkylstearate and a polysaccharide (hydroxyethylcellulose and methylhydroxypropylcellulose) and a mixture of fatty alcohols stearylic alcohol/béhenylic alcohol. Those emulsions do not permit to form soft-solid compositions.

The Applicant has discovered that this objective may be achieved with novel emulsions forming soft solid compositions, which are stable on storage, simultaneously having good cosmetic properties: soft feel and immediate dry sensation, non-wetting freshness, absence of tackiness and non-greasy feel, and good efficacy in the desired application.

This discovery forms the basis of the invention.

The present invention relates to a composition in the form of an oil-in-water emulsion, comprising, in a cosmetically acceptable medium:

A) a continuous aqueous phase and

B) an oily phase dispersed in the said aqueous phase and comprising at least one hydrocarbon-based oil;

C) at least one mixture consisting of:

i) at least one nonionic surfactant containing a saturated linear hydrocarbon-based chain comprising at least 16 carbon atoms, the said surfactant being other than a fatty alcohol, and ii) at least one fatty alcohol chosen from:

a pure fatty alcohol comprising more than 16 carbon atoms;

a mixture consisting exclusively of fatty alcohols containing at least 16 carbon atoms and comprising at least 50% by weight of fatty alcohol(s) containing at least 18 atoms; and D) at least one wax with a melting point of greater than 45° C. comprising one or more $C_{40}$-$C_{70}$ ester compounds and not comprising any $C_{20}$-$C_{39}$ ester compounds, in an amount from 1 to 10% by weight relative to the total weight of the composition and E) at least one water-soluble polysaccharide; the said composition having a hardness measured at 32° C. and at a humidity of 40% ranging from 20 kPa to 200 kPa and preferably ranging from 25 kPa to 150 kPa.

The present invention also relates to a cosmetic process for treating and/or caring for human keratin materials, characterized in that it consists in applying to the surface of the keratin material a composition as defined previously.

The present invention also relates to a cosmetic process for treating and/or caring for human keratin materials, characterized in that it consists in applying to the surface of the keratin material a composition as defined previously.

The present invention also relates to a cosmetic process for treating human perspiration and/or perspiration-related body odour, which consists in applying to the surface of a human keratin material a composition as defined previously comprising at least one deodourant active agent and/or one antiperspirant active agent.

Other subjects of the invention will emerge later in the description.

The expression "cosmetically acceptable" means compatible with the skin and/or its appendages or mucous membranes, having a pleasant colour, odour and feel and not causing any unacceptable discomfort (stinging, tautness or redness) liable to discourage the consumer from using this composition.

The expression "human keratin materials" means the skin (body, face, area around the eyes), hair, eyelashes, eyebrows, body hair, nails, lips or mucous membranes.

The term "antiperspirant" means any substance which has the effect of reducing the flow of sweat and/or of reducing the sensation of moisture associated with human sweat, and/or of masking human sweat.

The term "deodourant active agent" refers to any substance that is capable of masking, absorbing, improving and/or reducing the unpleasant odour resulting from the decomposition of human sweat by bacteria.

The term "fatty alcohol" means any non-alkoxylated alcohol comprising a linear saturated hydrocarbon-based chain, in particular consisting of a linear alkyl chain, the said chain comprising at least 10 carbon atoms and a hydroxyl function.

The term "hydrocarbon-based chain" means an organic group predominantly consisting of hydrogen atoms and carbon atoms.

The term "pure fatty alcohol comprising more than 16 carbon atoms" means any non-alkoxylated alcohol consisting of more than 95% by weight of the said alcohol; the said alcohol comprising a hydrocarbon-based chain, in particular consisting of a saturated linear alkyl chain comprising more than 16 carbon atoms and a hydroxyl function.

The term "mixture exclusively consisting of fatty alcohols comprising at least 16 carbon atoms" means any mixture comprising at least two non-alkoxylated alcohols comprising a linear saturated hydrocarbon-based chain, in particular consisting of a linear or branched alkyl chain, the said chain comprising at least 16 carbon atoms and a hydroxyl function; the said fatty alcohol mixture containing less than 1% by weight and preferably less than 0.5% by weight of $C_{12}$-$C_{15}$ fatty alcohol relative to the total weight of the fatty alcohol mixture, or even being free of $C_{12}$-$C_{15}$ fatty alcohol.

The term "ester compound" means any organic molecule comprising a linear or branched, saturated or unsaturated hydrocarbon-based chain comprising at least one ester function of formula —COOR in which R represents a hydrocarbon-based radical, in particular a saturated linear alkyl radical.

The term "wax not comprising any $C_{20}$-$C_{39}$ ester compounds" means any wax containing less than 1% by weight and preferably less than 0.5% by weight of $C_{20}$-$C_{39}$ ester compounds relative to the weight of the wax, or even being free of $C_{20}$-$C_{39}$ ester compounds.

Melting Point

For the purposes of the invention, the melting point corresponds to the temperature of the most endothermic peak observed in thermal analysis (DSC) as described in the standard ISO 11357-3; 1999. The melting point of the wax can be measured using a differential scanning calorimeter (DSC), for example the calorimeter sold under the name MDSC 2920 by TA Instruments.

The Measurement Protocol is as Follows:

A sample of 5 mg of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference between the power absorbed by the empty crucible and the power absorbed by the crucible containing the sample of surfactant or wax as a function of the temperature is measured. The melting point of the compound is the temperature value corresponding to the top of the peak of the curve representing the variation in the difference in power absorbed as a function of the temperature.

Hardness

The compositions according to the invention have a hardness measured at 32° C. and at a humidity of 40% ranging from 20 kPa to 200 kPa and preferably ranging from 25 kPa to 150 kPa.

The hardness is defined as the maximum stress force $F_{max}$ measured by texturometry during the penetration of a cylindrical probe into the sample of formula, assessed under precise measurement conditions as follows.

The formulae are poured hot into jars 9 cm in diameter and 3 cm deep (i.e.: "Favorit Soft" jars from RPC Bramlage GmbH). Cooling is carried out at room temperature. The hardness of the formulae produced is measured after an interval of 24 hours. The jars containing the samples are characterized by texturometry using a texturometer such as the TA-XT2 machine sold by the company Rheo, according to the following protocol:

At a temperature of 32° C. and at a relative humidity of 40%, a cylindrical stainless-steel probe with a spindle 2 cm in diameter is brought into contact with the sample at a speed of 1 mm/s. The measurement system detects the interface with the sample, with a detection threshold equal to 0.005 newton. The probe sinks 1 mm into the sample, at a rate of 0.1 mm/s. The measuring device records the change in the force measured in compression over time, during the penetration phase. The hardness of the sample corresponds to the mean of the maximum values of the force detected during the penetration, over at least three measurements. After a measurement, the relaxation time is 1 second, and the probe is withdrawn at a speed of 1 mm/s.

The hardness of the composition is calculated via the following equation:

$$\text{hardness} = \frac{F_{max}}{Cylindersurface}$$

Mixture of Surfactants and of Fatty Alcohol

Nonionic Surfactants

The nonionic surfactants in accordance with the invention contain a saturated linear hydrocarbon-based chain comprising at least 16 carbon atoms, preferably ranging from 16 to 26 and more preferentially from 16 to 22 carbon atoms.

Among the nonionic surfactants, examples that may be mentioned include:
- alkylpolyglucosides in which the alkyl chain comprises at least 16 carbon atoms;
- alkoxylated (preferably ethoxylated) fatty alcohols comprising at least 16 carbon atoms;
- polyglyceryl fatty esters containing a chain comprising at least 16 carbon atoms;
- mixtures thereof.

The alkylpolyglucosides generally correspond to the following structure:

R(O)(G)x in which the radical R is a linear alkyl radical containing at least 16 carbon atoms, preferably ranging from 16 to 26 and more preferentially from 16 to 22 carbon atoms, G is a saccharide residue and x ranges from 1 to 5, preferably from 1.05 to 2.5 and more preferentially from 1.1 to 2.

The saccharide residue may be chosen from glucose, dextrose, saccharose, fructose, galactose, maltose, maltotriose, lactose, cellobiose, mannose, ribose, dextran, talose, allose, xylose, levoglucan, cellulose and starch. More preferentially, the saccharide residue denotes glucose.

It should also be noted that each unit of the polysaccharide part of the alkylpolyglycoside may be in α or β isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

Among the alkylpolyglucosides that may be used according to the invention, mention may be made of arachidylpolyglucoside, such as that present in the commercial product Montanov 202® from the company SEPPIC, and cetearylglucoside, such as that in the commercial product Tegocare CG90® from the company Evonik.

Among the ethoxylated fatty alcohols that may be used according to the invention, mention may be made of Beheneth-10, such as the commercial product Eumulgin BA 10 from Cognis.

Among the polyglyceryl fatty esters, mention may be made of polyglyceryl-6 behenate, such as the commercial product Pelemol 6G22® from Phoenix Chemical or polyglyceryl-10 behenate/eicosadiate, such as the commercial product Nomcort HK-P® from Nisshin Oillio.

Use will be made more particularly of alkylpolyglucosides and preferably $C_{16}$-$C_{18}$ alkylpolyglucosides such as cetearylglucoside, and $C_{20}$-$C_{22}$ alkylpolyglucosides such as arachidylpolyglucoside, and more particularly arachidylpolyglucoside.

Fatty Alcohols

The fatty alcohols in accordance with the invention are chosen from:
- a pure fatty alcohol comprising more than 16 carbon atoms;
- a mixture of fatty alcohols containing at least 16 carbon atoms and comprising at least 50% by weight of fatty alcohol(s) containing at least 18 atoms.

Mixtures of fatty alcohols containing at least 18 atoms will be chosen more particularly.

The pure fatty alcohols in accordance with the invention containing more than 16 carbon atoms preferably comprise from 18 to 26 carbon atoms and more preferentially from 18 to 22 carbon atoms.

Among the pure fatty alcohols in accordance with the invention containing more than 16 carbon atoms, mention may be made of:
- stearyl alcohol, such as the commercial product Kalcol 80-98® from Kao,
- arachidyl alcohol, such as the commercial products Hainol 20SS® from the company Kokyu Alcohol Kogyo Co. Ltd and Nacol 20-95® from the company Sasol Germany GMBH (Hamburg),
- behenyl alcohol, such as the commercial products Nacol 22-97® and Nacol 22-98® from the company Sasol Germany GMBH (Hamburg),
- and mixtures thereof.

The mixtures of fatty alcohols in accordance with the invention containing more than 16 carbon atoms preferably comprise from 16 to 26 carbon atoms and more preferentially from 16 to 22 carbon atoms. They contain at least 50% fatty alcohol(s) comprising at least 18 carbon atoms, preferably from 50% to 100% and more preferentially from 70% to 100% by weight relative to the weight of the fatty alcohol mixture.

Among the mixtures of fatty alcohols in accordance with the invention containing at least 16 carbon atoms and at least 50% by weight relative to the weight of the fatty alcohol mixture, mention may be made of
- a cetearyl alcohol (mixture of cetyl alcohol and stearyl alcohol) comprising at least 50% by weight of stearyl alcohol relative to the weight of the fatty alcohol so mixture, such as the mixture comprising 70% by weight of $C_{18}$ fatty alcohol(s) and 30% by weight of $C_{16}$ fatty alcohol(s), such as the commercial product Nafol 1618 S® (Sasol Germany GmbH Hamburg),
- mixtures based on at least one $C_{22}$ fatty alcohol, at least one $C_{20}$ fatty alcohol and at least one $C_{18}$ fatty alcohol,
- a mixture of arachidyl alcohol and behenyl alcohol.

Among the mixtures based on at least one $C_{22}$ fatty alcohol, at least one $C_{20}$ fatty alcohol and at least one $C_{18}$ fatty alcohol, mention may be made of:

- the mixture comprising 77% by weight of $C_{22}$ fatty alcohol(s), 18% by weight of $C_{20}$ fatty alcohol(s) and 5% by weight of $C_{18}$ fatty alcohol(s), such as the commercial product Nafol 1822 C Alcohol® (Sasol Germany GmbH Hamburg) or the commercial product Lanette 22® (Cognis Corporation Care Chemicals);
- the mixture comprising 80% by weight of $C_{22}$ fatty alcohol(s), 10% by weight of $C_{20}$ fatty alcohol(s) and 10% by weight of $C_{18}$ fatty alcohol(s), such as the commercial product Behenyl Alcohol 80® (Kokyu Alcohol Kogyo Co. Ltd);
- the mixture comprising 44% by weight of $C_{22}$ fatty alcohol(s), 11% by weight of $C_{20}$ fatty alcohol(s) and 43% by weight of $C_{18}$ fatty alcohol(s), such as the commercial product Nafol 1822 Alcohol® (Sasol Germany GmbH Hamburg);
- the mixture comprising 6% by weight of $C_{24}$ fatty alcohol(s), 30% by weight of $C_{22}$ fatty alcohol(s), 58% by weight of $C_{20}$ fatty alcohol(s) and 7% by weight of $C_{18}$ fatty alcohol(s), such as the commercial product Nafol 20-22 EN (Sasol Germany GmbH Hamburg)

As mixture of nonionic surfactant and of fatty alcohol in accordance with the invention, use will preferentially be made of one of the following mixtures:

- a cetearyl alcohol (cetyl alcohol and stearyl alcohol) comprising at least 50% by weight of stearyl alcohol relative to the weight of the fatty alcohol mixture, cetearylglucoside such as that of the product Tegocare CG90® and behenyl alcohol,
- a cetearyl alcohol (cetyl alcohol and stearyl alcohol) comprising at least 50% by weight of stearyl alcohol relative to the weight of the fatty alcohol mixture, and cetearylglucoside such as that of the product Tegocare CG90®,
- a mixture of arachidyl alcohol, behenyl alcohol and arachidylglucoside, such as the commercial product Montanov 202® from the company SEPPIC.

Use will be made more particularly of a mixture of arachidyl alcohol and behenyl alcohol/arachidylglucoside, such as the commercial product Montanov 202® from the company SEPPIC.

The fatty alcohol/nonionic surfactant mixture is preferably present in the emulsions in accordance with the invention in active material concentrations ranging from 1% to 10% by weight and more preferentially from 2% to 7% by weight relative to the total weight of the emulsion.

The fatty alcohol/nonionic surfactant mixture preferably contains more than 50% by weight of fatty alcohol(s) and more preferentially more than 70% by weight of fatty alcohol(s) relative to the total weight of the said fatty alcohol/nonionic surfactant mixture.

Waxes

The wax under consideration in the context of the present invention is generally a lipophilic compound that is solid at room temperature (25° C.), with a solid/liquid reversible change of state, having a melting point of greater than or equal to 45° C., preferably ranging from 45 to 95° C. and more particularly ranging from 45 to 85° C.

The waxes that may be used in the compositions according to the invention are chosen from waxes with a melting point of greater than 45° C. comprising one or more $C_{40}$-$C_{70}$ ester compounds and not comprising any $C_{20}$-$C_{39}$ ester compounds.

The waxes according to the invention may also be used in the form of a mixture of waxes.

The content of ester comprising from 40 to 70 carbon atoms and preferably ranges from 20% to 100% by weight and preferably from 20% to 90% by weight relative to the total weight of wax(es).

Use will be made more particularly of candelilla wax and/or beeswax.

The composition according to the invention may comprise a wax content preferably ranging from 2% to 8% by weight relative to the total weight of the composition.

Water-Soluble Polysaccharides

The term "polysaccharide" means any polymer consisting of several saccharides (or monosaccharides) having the general formula:

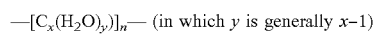

and linked together via O-oside bonds.

The water-soluble polysaccharides that may be used in the present invention are especially chosen from starches, gellans, scleroglucan gum, guar gum, konjac, agar, and celluloses such as hydroxyethylcellulose and hydroxypropylcellulose, and mixtures thereof.

Starches are preferentially used.

The "term water-soluble" means partially or totally soluble in water to give a gelled or thickened solution at a concentration of 1% active material in water, after implementation with or without heating.

The starches that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the botanical origin of the starches. The amylose/amylopectin weight ratio may range from 30/70 (corn) to 16/84 (rice). The molecular weight of the amylose is preferably up to 1 million by weight and that of the amylopectin is preferably from 100 to 500 million by weight.

The starch molecules used in the present invention may be unmodified or chemically or physically modified.

Their botanical origin may be cereals or tubers. Thus, the natural starches may be chosen from corn starch, rice starch, tapioca starch, cassava starch, barley starch, potato starch, wheat starch, sorghum starch, palm starch and pea starch.

Among the unmodified starches, mention may be made of unmodified corn starches (INCI name: *Zea mays* starch), for instance the products sold under the trade name Farmal CS®, in particular the commercial product Farmal CS 3650® from the company Corn Products International.

Mention may also be made of unmodified rice starches (INCI name: *Oryza sativa* (rice) starch), for instance the commercial product Remy DR I® sold by the company Beneo-Remy.

According to a particular form of the invention, starches used are modified by crosslinking with functional agents capable of reacting with the hydroxyl groups of the starch molecules, which will thus bond together (for example with glyceryl and/or phosphate groups).

Monostarch phosphates (of the type St-O—PO—(OX)$_2$), distarch phosphates (of the type St-O—PO—(OX)—O—St) or even tristarch phosphates (of the type St-O—PO—(O-St)$_2$) or mixtures thereof may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Use will preferentially be made of distarch phosphates or of compounds rich in distarch phosphate, in particular the distarch phosphate hydroxypropyl ethers having the INCI name: Hydroxypropyl Starch Phosphate, for instance the products sold under the trade names Farinex VA70 C or Farmal MS 689® from the company Avebe Stadex; the products sold under the trade names Structure BTC®, Structure HVS®, Structure XL® or Structure Zea® from National Starch (corn distarch phosphate).

Preferentially, the starch will be chosen from unmodified corn starches, unmodified rice starches and corn distarch phosphates, or mixtures thereof.

Even more preferentially, starch will be chosen from corn distarch phosphates.

According to the invention, the water-soluble polysaccharide(s) may preferably represent from 0.5% to 6% by weight and more particularly from 1% to 4% by weight relative to the total weight of the final composition.

Aqueous Phase

The term "aqueous phase" means a phase comprising water and generally any molecule in dissolved form in water in the composition.

The aqueous phase of the said compositions comprises water and generally other water-soluble or water-miscible solvents. The water-soluble or water-miscible solvents comprise monoalcohols with a short chain, for example of $C_1$-$C_4$, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol, glycerol and 1,3-propanediol will be used more particularly.

The concentration of the aqueous phase preferably ranges from 50% to 90% by weight and preferably from 60% to 90% by weight relative to the total weight of the composition.

Oily Phase

The compositions according to the invention contain at least one water-immiscible organic liquid phase, known as an oily phase. This phase generally comprises one or more hydrophobic compounds that make said phase water-immiscible. The said phase is liquid (in the absence of structuring agent) at room temperature (20-25° C.).

Preferentially, the water-immiscible organic-liquid organic phase in accordance with the invention generally comprises at least one volatile or non-volatile hydrocarbon-based oil and optionally at least one volatile or non-volatile silicone oil.

The term "oil" means a fatty substance that is liquid at room temperature (25° C.) and atmospheric pressure (760 mmHg, i.e. $10^5$ Pa). The oil may be volatile or non-volatile.

For the purpose of the invention, the term "volatile oil" means an oil that is capable of evaporating on contact with the skin or the keratin fibre in less than one hour, at room temperature and atmospheric pressure. The volatile oils of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oils in accordance with the invention are preferably chosen from any cosmetically acceptable oil, especially mineral, animal, plant or synthetic oils, especially hydrocarbon-based oils or silicone oils, or mixtures thereof.

The term "hydrocarbon-based oil" means an oil mainly containing carbon and hydrogen atoms and possibly one or more functions chosen from hydroxyl, ester, ether and carboxylic functions. Generally, the oil has a viscosity of from 0.5 to 100 000 mPa·s and preferably from 50 to 50 000 mPa·s and more preferably from 100 to 30 000 mPa·s.

The term "silicone oil" means an oil comprising in its structure carbon atoms and at least one silicon atom.

As examples of volatile hydrocarbon-based oils that may be used in the invention, mention may be made of:

volatile hydrocarbon-based oils chosen from hydrocarbon-based oils containing from 8 to 16 carbon atoms, and in particular $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in patent application DE 10 2008 012 457 from Cognis.

Among the volatile hydrocarbon-based oils, use will preferably be made of alkanes such as isohexadecane and isododecane.

As examples of non-volatile hydrocarbon-based oils that may be used in the invention, mention may be made of:

hydrocarbon-based plant oils, such as liquid triglycerides of fatty acids of 4 to 24 carbon atoms, such as heptanoic or octanoic acid triglycerides, or else wheatgerm oil, olive oil, sweet almond oil, palm oil, rapeseed oil, cottonseed oil, alfalfa oil, poppy seed oil, pumpkin seed oil, marrow oil, blackcurrant oil, evening primrose oil, millet oil, barley oil, quinoa oil, rye oil, safflower oil, candlenut oil, passionflower oil, musk rose oil, sunflower oil, corn oil, soybean oil, marrow oil, grape seed oil, sesame oil, hazelnut oil, apricot oil, macadamia oil, castor oil, avocado oil, caprylic/capric acid triglycerides, such as those sold by Stéarineries Dubois or those sold under the names Miglyol 810, 812 and 818 by Dynamit Nobel, jojoba oil or shea butter oil;

synthetic ethers containing from 10 to 40 carbon atoms such as dicaprylyl ether;

synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, C₁₂-C₁₅ alkyl benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

linear or branched hydrocarbons, of mineral or synthetic origin, such as liquid paraffins and derivatives thereof, petroleum jelly, polydecenes, polybutenes, hydrogenated polyisobutene such as Parleam, and squalane, fatty alcohols which are liquid at room temperature and which comprise a branched and/or unsaturated carbon-based chain containing from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates;

acetates;

citrates.

Among the volatile silicones, mention may be made of volatile linear or cyclic silicone oils, especially those with a viscosity ≤8 centistokes ($8\times10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general formula (I):

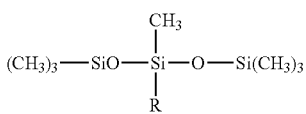

in which R represents an alkyl group containing from 2 to 4 carbon atoms, of which one or more hydrogen atoms may be substituted with a fluorine or chlorine atom.

As examples of non-volatile silicone oils, mention may be made of linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof. Use will be made more particularly of a linear non-volatile polydimethylsiloxane (PDMS).

Preferably, the oily phase comprises at least one non-volatile hydrocarbon-based oil and optionally at least one non-volatile silicone oil.

The non-volatile hydrocarbon-based oil will preferably be chosen from triglycerides, such as caprylic/capric acid triglycerides, fatty acid esters such as isopropyl palmitate, isononyl isononanoate or isostearyl isostearate, ethers such as dicaprylyl ether, and mixtures thereof, and more particularly isopropyl palmitate and isononyl isononanoate, such as the commercial product Dub IPP® sold by the company Stéarineries Dubois.

The hydrocarbon-based oil(s) will preferably be present in the composition in concentrations ranging from 5% to 30% by weight and more preferentially ranging from 5% to 20% by weight relative to the total weight of the composition.

The concentration of the oily phase preferably ranges from 10% to 30% relative to the total weight of the composition.

According to a particular form of the invention, the composition may also contain at least one nonionic associative polymer and/or a diester of polyethylene glycol and of a fatty acid.

Associative Nonionic Polymer

According to a particularly preferred form, the compositions also comprise at least one nonionic associative polymer.

For the purposes of the present invention, the term "associative polymers" means hydrophilic polymers that are capable, in an aqueous medium, of reversibly associating with each other or with other molecules. Their chemical structure more particularly comprises at least one hydrophilic region and at least one hydrophobic region.

The term "hydrophobic group" is understood to mean a radical or polymer comprising a saturated or unsaturated and linear or branched hydrocarbon-based chain. When the hydrophobic group denotes a hydrocarbon-based radical, it comprises at least 10 carbon atoms, preferably from 10 to 30 carbon atoms, in particular from 12 to 30 carbon atoms and more preferentially from 18 to 30 carbon atoms. Preferentially, the hydrocarbon-based group is derived from a monofunctional compound.

By way of example, the hydrophobic group may be derived from a fatty alcohol, such as stearyl alcohol, dodecyl alcohol or decyl alcohol, or else from a polyoxyalkylenated fatty alcohol, such as Steareth-100. It may also denote a hydrocarbon-based polymer, for instance polybutadiene.

The nonionic associative polymers may be chosen from:

celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon, celluloses modified with alkylphenyl polyalkylene glycol ether groups, such as the product Amercell Polymer HM-1500 (nonylphenyl polyethylene glycol (15) ether) sold by the company Amerchol, guars such as hydroxypropyl guar, modified with groups comprising at least one fatty chain such as an alkyl chain, inulins modified with groups comprising at least one fatty chain, such as alkyl carbamate inulins and in particular the lauryl carbamate inulin sold by the company Orafti under the name Inutec SP1, diesters of polyethylene glycol and of a fatty acid, such as polyethylene glycol (150 OE) distearate, for instance PEG-150 distearate sold under the trade name Emcol L 32-45® by Witco, associative polyurethanes.

Associative polyurethanes are nonionic block copolymers comprising in the chain both hydrophilic blocks usually of polyoxyethylene nature (polyurethanes may also be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be provided. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to a preferred embodiment, a nonionic associative polymer of polyurethane type is used as gelling agent.

As examples of nonionic fatty-chain polyurethane polyethers that may be used in the invention, it is also possible to use Rheolate® FX 1100 (Steareth-100/PEG 136/HDI (hexamethyl diisocyanate) copolymer), Rheolate® 205® containing a urea function, sold by the company Elementis, or Rheolate® 208, 204 or 212, and also Acrysol RM 184® or Acrysol RM 2020®.

Mention may also be made of the product Elfacos T210® containing a C12-C14 alkyl chain, and the product Elfacos T212® containing a C16-18 alkyl chain (PPG-14 Palmeth-60 Hexyl Dicarbamate) from Akzo.

The product DW 1206B® from Röhm & Haas containing a C20 alkyl chain and a urethane bond, sold at a solids content of 20% in water, may also be used.

Use may also be made of solutions or dispersions of these polymers, especially in water or in aqueous-alcoholic medium. Examples of such polymers that may be mentioned are Rheolate® 255, Rheolate® 278 and Rheolate® 244 sold by the company Elementis. Use may also be made of the products DW 1206F and DW 1206J sold by the company Röhm & Haas.

The associative polyurethanes that may be used according to the invention are in particular those described in the article by G. Fonnum, J. Bakke and Fk. Hansen-Colloid Polym. Sci., 271, 380-389 (1993).

Even more particularly, according to the invention, use may also be made of a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Röhm & Haas under the names Aculyn 46® and Aculyn 44®. Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Use may also be made of solutions or dispersions of these polymers, especially in water or in aqueous-alcoholic medium. Examples of such polymers that may be mentioned include Rheolate FX1010®, Rheolate FX1035® and Rheolate 1070® from the company Elementis, and Rheolate 255®, Rheolate 278® and Rheolate 244® sold by the company Elementis. Use may also be made of the products Aculyn 44, Aculyn 46®, DW 1206F® and DW 1206J®, and also Acrysol RM 184 from the company Röhm & Haas, or alternatively Borchigel LW 44® from the company Borchers, and mixtures thereof.

Use will be made more particularly of an associative nonionic polyurethane polyether such as the product sold especially by the company Elementis under the name Rheolate FX 1100®, which is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 30 000 (INCI name: PEG-136/Steareth-100 I/SMDI Copolymer).

The amount of associative nonionic polymer(s) as active material may range, for example, from 0.1% to 10% by weight, preferably from 0.25% to 6% by weight and better still from 0.5% to 3% by weight relative to the total weight of the composition.

Additives

The compositions according to the invention may also furthermore comprise additional cosmetic and dermatological active agents.

The cosmetic compositions according to the invention may comprise cosmetic adjuvants chosen from opacifiers, stabilizers, preserving agents, polymers, fragrances, thickeners, sunscreens, dermatological or cosmetic active agents, fillers, suspension agents, dyestuffs or any other ingredient usually used in cosmetics for this type of application.

Among the fillers, mention may be made of talc, kaolin, silicas, clays, perlite and water-insoluble particulate starches.

Among the silicas, mention may be made of:

Among the silicas, mention may be made of:

porous silica microspheres, especially porous silica microspheres. The porous spherical silica microparticles preferably have a mean particle size ranging from 0.5 to 20 μm and more particularly from 3 to 15 μm. They preferably have a specific surface area ranging from 50 to 1000 m$^2$/g and more particularly from 150 to 800 m$^2$/g. They preferably have a specific pore volume ranging from 0.5 to 5 ml/g and more particularly from 1 to 2 ml/g. As examples of porous silica microbeads, use may be made of the following commercial products:

Silica Beads SB 150® from Miyoshi

Sunsphere H-51®; Sunsphere H53® and Sunsphere H33® from Asahi Glass MSS-500-3H® from the company Kobo Sunsil 130® from Sunjin Spherica P-1500® from Ikeda Corporation Sylosphere® from Fuji Silysia;

polydimethylsiloxane-coated amorphous silica microspheres, especially those sold under the name SA Sunsphere® H33, amorphous hollow silica particles, especially those sold under the name Silica Shells by the company Kobo.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

The dermatological or cosmetic active agents may be chosen especially from moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents, keratolytic agents, agents for preventing hair regrowth and antiacne agents.

Galenical Forms

The compositions according to the invention are in the form of a soft solid stick whose consistency may vary as a function of the desired application, the region of human keratin material to be treated and the desired conditioning, such as a cosmetic product for caring for, holding or colouring the skin or the hair, or a body hygiene product, especially such as a deodourant and/or antiperspirant.

Conditioning

The compositions of the invention may especially be conditioned in a tube, in a device equipped with a perforated wall, especially a grille. In this regard, they comprise the ingredients generally used in products of this type, which are well known to a person skilled in the art.

Deodourant and/or Antiperspirant Compositions

The present invention also relates to a cosmetic process for treating human perspiration and/or perspiration-related body odour, which consists in applying to the surface of a human keratin material a composition as defined previously comprising at least one deodourant active agent and/or one antiperspirant active agent.

The compositions in accordance with the invention may thus be used as deodorants and/or antiperspirants and may contain at least one deodorant active agent and/or one antiperspirant active agent.

Additional Antiperspirant Salts or Complexes

The aluminium and/or zirconium antiperspirant salts or complexes are preferably chosen from aluminium halohydrates; aluminium zirconium halohydrates, complexes of zirconium hydroxychloride and of aluminium hydroxychloride with or without an amino acid, such as those described in U.S. Pat. No. 3,792,068.

Among the aluminium salts, mention may be made in particular of aluminium chlorohydrate in activated or unactivated form, aluminium chlorohydrex, the aluminium chlorohydrex-polyethylene glycol complex, the aluminium chlorohydrex-propylene glycol complex, aluminium dichlorohydrate, the aluminium dichlorohydrex-polyethylene glycol complex, the aluminium dichlorohydrex-propylene glycol complex, aluminium sesquichlorohydrate, the aluminium sesquichlorohydrex-polyethylene glycol complex, the aluminium sesquichlorohydrex-propylene glycol complex, aluminium sulfate buffered with sodium aluminium lactate.

Among the aluminium-zirconium salts, mention may be made in particular of aluminium zirconium octachlorohydrate, aluminium zirconium pentachlorohydrate, aluminium zirconium tetrachlorohydrate and aluminium zirconium trichlorohydrate.

The complexes of zirconium hydroxychloride and of aluminium hydroxychloride with an amino acid are generally known as ZAG (when the amino acid is glycine). Among these products, mention may be made of the aluminium zirconium octachlorohydrex-glycine complexes, the aluminium zirconium pentachlorohydrex-glycine complexes, the aluminium zirconium tetrachlorohydrex-glycine complexes and the aluminium zirconium trichlorohydrex-glycine complexes.

The aluminium and/or zirconium antiperspirant salts or complexes may be present in the composition according to the invention in a proportion of at least 0.5% by weight and preferably from 0.5% to 25% by weight relative to the total weight of the composition.

Deodorant Active Agents

The compositions according to the invention may also furthermore contain one or more additional deodorant active agents.

The term "deodorant active agent" refers to any substance that is capable of masking, absorbing, improving and/or reducing the unpleasant odour resulting from the decomposition of human sweat by bacteria.

The deodorant agents may be bacteriostatic agents or bactericides that act on underarm odour microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise), glycerol derivatives, for instance caprylic/capric glycerides (Capmul MCM from Abitec), glyceryl caprylate or caprate (Dermosoft GMCY and Dermosoft GMC, respectively from Straetmans), polyglyceryl-2 caprate (Dermosoft DGMC from Straetmans), and biguanide derivatives, for instance polyhexamethylene biguanide salts; chlorhexidine and salts thereof; 4-phenyl-4,4-dimethyl-2-butanol (Symdeo MPP from Symrise); cyclodextrins.

Among the deodorant active agents in accordance with the invention, mention may also be made of zinc salts, for instance zinc salicylate, zinc gluconate, zinc pidolate; zinc sulfate, zinc chloride, zinc lactate, zinc phenolsulfonate; zinc ricinoleate;

sodium bicarbonate;

salicylic acid and derivatives thereof such as 5-n-octanoylsalicylic acid;

zeolites, especially silver-free metallic zeolites;

alum;

triethyl citrate.

The deodorant active agents may preferably be present in the compositions according to the invention in weight concentrations ranging from 0.01% to 10% by weight relative to the total weight of the composition.

The examples that follow serve to illustrate the present invention. The amounts are given as mass percentages relative to the total weight of the composition.

EXAMPLES

The examples were prepared according to the following protocol:
- the aqueous phase containing the gelling agents or thickeners and the aluminium salts is heated to 80° C.;
- the waxes and the surfactant mixture are heated with the oils to 80° C.;
- the two phases are mixed together and sheared in a Rayneri blender for 10 minutes;
- the filler is then added while mixing with a Rayneri deflocculator;
- the composition is hot-cast into the packs.

The appearance and the homogeneity of the products are evaluated visually 24 hours after manufacture.

Examples 1 and 2: Sensory Tests

| Phase | Ingredients | Composition 1 (invention) Soft solid O/W emulsion |
|---|---|---|
| A | Arachidylglucoside/behenyl alcohol/arachidyl alcohol (Montanov 202 ®) | 3 |
|   | Isopropyl palmitate (Palmitate Dub IPP ®) | 10 |
|   | Dimethicone (10 cSt) (Element14 PDMS 10-A ®) | 10 |
|   | *Euphorbia cerifera* (candelilla) wax (Candelilla Wax SP 75 G ®) | 3 |
|   | Fragrance | 1 |
| B | *Zea mays* (corn) starch (Corn starch B) | 3 |
|   | *Oryza sativa* (rice) starch (Remy DR I ®) | 1.5 |
|   | 50% aluminium chlorohydrate solution (Chlorhydrol 50 ®) | 30 |
|   | Steareth-100/PEG-136/HDI copolymer (Rheolate FX 1100 ®) | 0.5 |
|   | Preserving agent | 0.075 |
|   | Water | qs 100 |

The composition was compared with composition 2 (outside the invention) corresponding to the commercial antiperspirant product sold under the name: Secret Clinical Strength Antiperspirant/Deodourant® which is an anhydrous soft solid composition.

List of Ingredients Indicated on the Conditioning:
Aluminium zirconium trichlorohydrex GLY (20%)
CyclopentasiloxaneCyclopentasiloxaneCyclopentasiloxane
Dimethicone
Tribehenin
Petrolatum
Cyclodextrin
C18-36 acid triglyceride
Fragrance
PPG-14 butyl ether Sensory Test Protocol
Parameters: Cosmetic qualities and defects of the formulations
Experimental programme: Sequential monadic (use of one product at a time for three consecutive days), random distribution
Panel: 11 women, from 25 to 60 years old, daily users of roll-on antiperspirant.

The products presented in grille sticks are evaluated under the armpits with free application (at home).
Feedback is given after 4 days of use of each formulation.
At the end of the test, 7 out of the 11 women preferred formulation 1 for its ease of application and its faster drying. Composition 1 according to the invention has a creamier, less thick texture, is more glidant on the armpit and penetrates more easily.

Examples 3 to 5: Influence of the Choice of Wax

Formulations 3 to 5 below were prepared:

| Phase | Ingredients | Example 3 (invention) | Comparative Example 4 with carnauba wax | Comparative Example 5 with polyethylene wax |
|---|---|---|---|---|
| A | Arachidylglucoside/behenyl alcohol/arachidyl alcohol (Montanov 202 ®) | 3 | 3 | 3 |
|   | Isopropyl palmitate (Palmitate Dub IPP ®) | 10 | 10 | 10 |
|   | Dimethicone (10 cSt) (Element14 PDMS 10-A ®) | 10 | 10 | 10 |
|   | *Euphorbia cerifera* (candelilla) wax (Candelilla Wax SP 75 G ®) | 3 | — | — |
|   | Carnauba wax | — | 3 | — |
|   | Polyethylene (Cirebelle 108 ®) | — | — | 3 |
| B | *Oryza sativa* (rice) starch (Remy DR I ®) | 1.5 | 1.5 | 1.5 |
|   | 50% aluminium chlorohydrate solution (Chlorhydrol 50) | 30 | 30 | 30 |
|   | Preserving agent | 0.075 | 0.075 | 0.075 |
|   | Water | qs 100 | qs 100 | qs 100 |
| C | *Zea mays* (corn) starch (Corn starch B) | — | — | 3 |
| Hardness (kPa) | | 74 | Not measurable | Not measurable |
| Appearance and stability after 24 hours at 25° C. | | Soft solid Stable | Creaming 24 h | Soft cream Stable |

A formulation 3 according to the invention comprising, as wax, candelilla wax with a melting point of 64.3° C. and a $C_{42}$-$C_{64}$ ester content of 22-32% was compared with:
- a formulation 4 outside the invention comprising esters containing less than 30 carbons;
- a formulation 5 outside the invention comprising an ester-free polyethylene wax.

Examples 3 to 5 were prepared under the same conditions as Example 1. Stability test conditions to be completed The results showed that formulation 3 according to the invention comprising candelilla wax has a soft solid appearance and remains stable after 24 hours at 25° C., in contrast with formulation 4 comprising an ester containing less than 30 carbons and formulation 5 with polyethylene wax.

Examples 6 to 10: Influence of the Choice of the Nonionic Surfactant/Fatty Alcohol Mixture The following emulsions were prepared, each comprising an alkylpolyglycoside/fatty alcohol mixture and, as common wax: beeswax with a melting point of 62° C. and a content of ester containing at least 40 carbon atoms of 71% by weight.

| Phase | Ingrédients | Exemple 6 (invention) | Exemple 7 (invention) | Exemple 8 (invention) |
|---|---|---|---|---|
| | ARACHIDYLGLUCOSIDE/ALCOOL BEHENYLIQUE/ALCOOL ARACHIDYLIQUE (MONTANOV 202 ®) | 3 | — | — |
| | CÉTÉARYLGLUCOSIDE (TEGOCARE CG90 ®) | — | 0.6 | 0.6 |
| | CETYLIC ALCOHOL | — | — | 2.4 |
| | MIXTURE OF C18/C20/C22 5/18/77LINEAR ALCOHOLS LINEAIRES (NAFOL 1822 C ®) | — | 2.4 | — |
| | DIMETHICONE (10 CST) (ELEMENT14 PDMS 10-A ®) | 10 | 10 | 10 |
| | ISOPROPYL PALMITATE (DUB IPP ®) | 10 | 10 | 10 |
| | BEESWAX (GR B 889 ®) | 3 | 3 | 10 |
| B | HYDROXYPROPYL STARCH PHOSPHATE (STRUCTURE XL ®) | 1 | 1 | 1 |
| | STEARETH-100/PEG-136/HDI COPOLYMER (RHEOLATE FX 1100 ®) | 0.5 | 0.5 | 0.5 |
| | 50% ALUMINIUM CHLOROHYDRATE SOLUTION (CHLORHYDROL 50 ®) | 20 | 20 | 20 |
| | PRESERVATIVE | 0.075 | 0.075 | 0.075 |
| | WATER | qsp 100 | qsp 100 | qsp 100 |
| C | SILICA (SUNSPHERE H 51 ®) | 3 | 3 | 3 |
| | Hardness (kPa) | 103 | 44 | 67 |
| | Appearance | Soft-solid | Soft-solid | Soft-solid |
| | Stability after 24 hours at 25° C. | Stable | Stable | Stable |

| Phase | Ingredients | Example 9 (outside the invention) | Example 10 (outside the invention) |
|---|---|---|---|
| A | Mixture of cetylstearyl glucoside and of cetyl and stearyl alcohols (12/46/42) (Montanov 68 ®) | 3 | — |
| | $C_{14}$-$C_{22}$ alcohol/$C_{12}$-$C_{20}$ alkylpolyglucoside (Montanov L ®) | — | 3 |
| | Dimethicone (10 cSt) (Element14 PDMS 10-A ®) | 10 | 10 |
| | Isopropyl palmitate (Dub IPP ®) | 10 | 10 |
| | Beeswax (White beeswax GR B 889 ®) | 3 | 3 |
| B | Hydroxypropyl starch phosphate (Structure XL ®) | 1 | 1 |
| | Steareth-100/PEG-136/HDI copolymer (Rheolate FX 1100 ®) | 0.5 | 0.5 |
| | 50% aluminium chlorohydrate solution (Chlorhydrol 50) | 20 | 20 |
| | Preserving agent | 0.075 | 0.075 |
| | Water | qs 100 | qs 100 |
| C | Silica (Sunsphere H 51 ®) | 3 | 3 |
| | Hardness (kPa) | 11 | 14 |
| | Appearance and stability after 24 hours at 25° C. | Creaming at 24 h | Creaming at 24 h |

Examples 6 to 10 were prepared under the same conditions as Example 1 and their stability was controlled according to the method indicated in the same Example 1.

The results showed that Examples 6 to 8 according to the invention comprising mixture of a nonionic surfactant and a mixture of fatty alcohols comprising at least 16 carbon atoms and comprising at least 50% by weight of fatty alcohol(s) comprising at least 18 carbon atoms are soft solids that are stable on storage, in contrast with:

1) composition 9 containing a mixture of nonionic surfactant and a mixture of fatty alcohols comprising 46% by weight of $C_{18}$ fatty alcohol (Montanov 68®);

2) example 10 containing a mixture of nonionic surfactant and a mixture of fatty alcohols comprising at least one $C_{14}$ fatty alcohol (Montanov L®).

Examples 6 and 11: Influence of the Presence of Polysaccharide

| Phase | Ingredients | Example 6 (invention) | Example 11 without starch (outside the invention) |
|---|---|---|---|
| A | Arachidylglucoside/behenyl alcohol/arachidyl alcohol (Montanov 202 ®) | 3 | 3 |
| | Dimethicone (10 cSt) (Element14 PDMS 10-A ®) | 10 | 10 |
| | Isopropyl palmitate (Dub IPP ®) | 10 | 10 |
| | Beeswax (White beeswax GR B 889 ®) | 3 | 3 |
| B | Hydroxypropyl starch phosphate (Structure XL ®) | 1 | — |
| | Steareth-100/PEG-136/HDI copolymer (Rheolate FX 1100 ®) | 0.5 | 0.5 |
| | 50% aluminium chlorohydrate solution (Chlorhydrol 50 ®) | 20 | 20 |
| | Preserving agent | 0.075 | 0.075 |
| | Water | qs 100 | qs 100 |
| | Hardness (kPa) | 103 | Not measurable |
| | Appearance and stability after 24 hours at 25° C. | Soft solid Stable | Creaming 24 h |

Examples 6 and 11 were prepared under the same conditions as Example 1 and their stability was controlled according to the method indicated in the same Example 1. The results showed that Example 6 of the invention comprising a starch was soft-solid and stable on storage, in contrast with Example 11 which is starch-free.

Examples 12 and 13: Influence of the Oily Phase

| Phase | Ingredients | Example 12 without hydrocarbon-based oil (outside the invention) | Example 13 with hydrocarbon-based oil (invention) |
|---|---|---|---|
| A | Behenylglycoside/behenyl alcohol (Montanov 202 ®) | 3 | 3 |
|  | Dimethicone (10 cSt) (Element14 PDMS 10-A ®) | 20 | — |
|  | Isopropyl palmitate (Dub IPP ®) | — | 20 |
|  | Beeswax (White beeswax GR B 889 ®) | 3 | 3 |
| B | Hydroxypropyl starch phosphate (Structure XL ®) | 1 | 1 |
|  | Steareth-100/PEG-136/HDI copolymer (Rheolate FX 1100 ®) | 0.5 | 0.5 |
|  | 50% aluminium chlorohydrate solution (Chlorhydrol 50) | 20 | 20 |
|  | Preserving agent | 0.075 | 0.075 |
|  | Water | qs 100 | qs 100 |
| C | Silica (Sunsphere H 51 ®) | 3 | 3 |
| Hardness (kPa) | | Not measurable | 22 |
| Appearance and stability after 24 hours at 25° C. | | Creaming at 24 h | Soft solid Stable |

Examples 12 and 13 were prepared under the same conditions as Example 1 and their stability was controlled according to the method indicated in the same Example 1.

The results showed that Example 13 of the invention comprising a hydrocarbon-based oil was soft-solid and stable on storage, in contrast with Example 12 which is free of hydrocarbon-based oil.

| Phase | Ingrédients | Exemple 14 (outside the invention) |
|---|---|---|
| A | BEHENYL GLYCOSIDE/ALCOOL BEHENYLIQUE (MONTANOV 202 ®) | 3 |
|  | DIMETHICONE (10 CST) (ELEMENT14 PDMS 10-A ®) | 10 |
|  | ISOPROPYL PALMITATE (DUB IPP ®) | 10 |
|  | C20-C40 ALKYL STEARATE KESTERWACHS | 3 |
| B | HYDROXYPROPYL STARCH PHOSPHATE (STRUCTURE XL ®) | 1 |
|  | STEARETH-100/PEG-136/HDI COPOLYMER (RHEOLATE FX 1100 ®) | 0.5 |
|  | ALUMINUM CHLOROHYDRATE EN SOLUTION A 50% (CHLORHYDROL 50) | 20 |
|  | PRESERVATIVES | 0.6 |
|  | WATER | qsp 100 |
| C | SILICA (SUNSPHERE H 51 ®) | 3 |
| Hardness (kPa) | | 7 |
| Appearance and stability after 24 hours at 25° C. | | Creaming after 24 h |

Example 14 was prepared under the same conditions as Example 1 and its stability was controlled according to the method indicated in the same Example 1.

The results showed that Example 14 outside the invention comprising, as a wax, a $C_{20}$-$C_{40}$ alkyl Stearate Kesterwachs is unstable on storage and is not soft-solid.

| Phase | Ingredients | Example 15 (invention) | Example 16 (outside the invention) |
|---|---|---|---|
| A | C14-C22 ALCOOL/C12-C20 ALKYLPOLYGLUCOSIDE (MONTANOV L ®) | 3 | 3 |
|  | DIMETHICONE (10 CST) (ELEMENT14 PDMS 10-A ®) | 10 | 10 |
|  | ISOPROPYL PALMITATE (DUB IPP ®) | 10 | 10 |
|  | *EUPHORBIA CERIFERA* (CANDELILLA) WAX (CANDELILLA WAX SP 75 G ®) | 3 | 0.6 |
| B | HYDROXYPROPYL STARCH PHOSPHATE (STRUCTURE XL ®) | 1 | 1 |
|  | STEARETH-100/PEG-136/HDI COPOLYMER (RHEOLATE FX 1100 ®) | 0.5 | 0.5 |
|  | ALUMINUM CHLOROHYDRATE EN SOLUTION A 50% (CHLORHYDROL 50) | 20 | 20 |
|  | CONSERVATEUR | 0.075 | 0.075 |
|  | EAU | qsp 100 | qsp 100 |
| C | SILICA (SUNSPHERE H 51 ®) | 3 | 3 |
| Hardness (kPa) | | 43 | 2 |
| Appearance and stability after 24 hours at 25° C. | | Soft-solid Stable | Creaming after 24 h and decantation of the silica |

Examples 15 and 16 were prepared under the same conditions as Example 1 and their stability was controlled according to the method indicated in the same Example 1.

The results showed that Example 15 of the invention comprising Candelilla Wax at 3% by weight was soft-solid and stable on storage, in contrast with Example 16 comprising Candelilla Wax in an amount less than 1% by weight (0.6%).

| Ingredients | Exemple 17 according to example 4 of EP2436369 (outside the invention) |
|---|---|
| WATER | qsp 100 |
| XANTHAN GUM | 0.05 |
| CARBOMER | 0.10 |
| GLYCERIN | 3.00 |
| BUTYLENE GLYCOL | 8.00 |
| PHENOXYETHANOL | 0.50 |
| SODIUM CITRATE | 0.09 |
| POLYVINYL ALCOHOL | 0.20 |
| SODIUM METHYL COCOYL TAURATE | 0.20 |
| CITRIC ACID | 0.01 |
| GLYCERYL STEARATE SE | 0.30 |
| DIMETHICONE | 1.00 |
| AERYTHRITYL TETRAETHYL-HEXANOATE | 2.00 |
| MINERAL OIL | 4.50 |
| *EIS GUINEENSIS* (PALM) OIL | 0.50 |
| BEHENYL ALCOHOL | 0.80 |
| CANDELLILA WAX | 0.20 |
| MICROCRYSTALLINE WAX | 0.08 |
| POLYETHYLENE WAX | 0.32 |
| Hardness (kPa) | Not measurable |
| Appearence | Fluid, shiny, smooth cream |

Example 17 was prepared under the same conditions as Example 1.

The invention claimed is:

1. Composition in the form of a soft solid oil-in-water emulsion comprising, in a cosmetically acceptable medium:
   A) a continuous aqueous phase and
   B) an oily phase dispersed in the said aqueous phase and comprising at least one hydrocarbon-based oil;
   C) at least one mixture consisting of:
      i) at least one nonionic surfactant containing a saturated linear hydrocarbon-based chain comprising at least 16 carbon atoms, the said surfactant being other than a fatty alcohol, and
      ii) at least one fatty alcohol selected from the group consisting of
         a pure fatty alcohol comprising more than 16 carbon atoms; and
         a mixture consisting exclusively of fatty alcohols containing at least 16 carbon atoms and comprising at least 50% by weight of fatty alcohol containing at least 18 atoms relative to the weight of the fatty alcohol mixture;
   D) at least one wax with a melting point of greater than 45° C. comprising one or more $C_{40}$-$C_{70}$ ester compounds and not comprising any $C_{20}$-$C_{39}$ ester compounds, in an amount from 1 to 10% by weight relative to the total weight of the composition and
   E) at least one water-soluble polysaccharide; the said composition having a hardness measured at 32° C. and at a humidity of 40% ranging from 20 kPa to 200 kPa.

2. Composition according to claim 1, wherein the nonionic surfactant is selected from the group consisting of
   alkylpolyglucosides in which the alkyl chain comprises at least 16 carbon atoms;
   ethoxylated fatty alcohols comprising at least 16 carbon atoms;
   polyglyceryl fatty esters containing a chain comprising at least 16 carbon atoms; and
   mixtures thereof.

3. Composition according to claim 1, wherein the nonionic surfactant with a hydrocarbon-based chain comprising at least 16 carbon atoms is an alkylpolyglycoside.

4. Composition according to claim 1, in which the fatty alcohol is selected from the group consisting of:
   (i) pure fatty alcohols selected from the group consisting of: stearyl alcohol, behenyl alcohol, arachidyl alcohol, and mixtures thereof; and
   (ii) mixtures of fatty alcohols selected from the group consisting of:
      a cetearyl alcohol comprising at least 50% by weight of stearyl alcohol relative to the weight of the fatty alcohol mixture,
      mixtures based on at least one $C_{22}$ fatty alcohol, at least one $C_{20}$ fatty alcohol and at least one $C_{18}$ fatty alcohol, and
      a mixture of behenyl alcohol and arachidyl alcohol.

5. Composition according to claim 1, wherein the mixture of nonionic surfactant and of fatty alcohol is selected from the group consisting of:
   a mixture of cetearyl alcohol comprising at least 50% by weight of stearyl alcohol relative to the weight of the fatty alcohol mixture, cetearylglucoside and behenyl alcohol,
   a mixture comprising at least one cetearyl alcohol comprising at least 50% by weight of stearyl alcohol relative to the weight of the fatty alcohol mixture and cetearylglucoside, and
   a mixture of arachidyl alcohol, behenyl alcohol and arachidylglucoside.

6. Composition according to claim 5, wherein the mixture of nonionic surfactant and of fatty alcohol is a mixture of behenyl alcohol, arachidyl alcohol and arachidylpolyglucoside.

7. Composition according to claim 1, wherein the wax is selected from the group consisting of candelilla wax, rice bran wax, beeswax and sunflower wax, and mixtures thereof.

8. Composition according to claim 1, wherein that the hydrocarbon-based oil(s) are present in concentrations ranging from 5% to 30% by weight relative to the total weight of the composition.

9. Composition according to claim 1, wherein the oily phase comprises at least one non-volatile hydrocarbon-based oil and optionally at least one non-volatile silicone oil.

10. Composition according to claim 9, in which the non-volatile hydrocarbon-based oil is selected from the group consisting of triglycerides, fatty acid esters, ethers and mixtures thereof.

11. Composition according to claim 1, wherein the concentration of the oily phase ranges from 10% to 30% relative to the total weight of the composition and the concentration of the aqueous phase ranges from 50% to 90% relative to the total weight of the composition.

12. Composition according to claim 1, wherein the water-soluble polysaccharide is a starch.

13. Composition according to claim 12, in which the starch is a distarch phosphate.

14. Composition according to claim 1, wherein the water-soluble polysaccharide(s) represent from 0.5% to 6% by weight relative to the total weight of the composition.

15. Composition according to claim 1, wherein the wax (es) with a melting point of greater than 45° C. comprising one or more $C_{40}$-$C_{70}$ ester compounds and not comprising any $C_{20}$-$C_{39}$ ester compounds represent from 2 to 8% by weight relative to the total weight of the composition.

16. Composition according to claim 1, which further comprises at least one nonionic associative polymer.

17. Composition according to claim 1, which further comprises at least one antiperspirant active agent and/or one deodorant active agent.

18. Cosmetic process for treating and/or caring for human keratin materials, which comprises applying to the surface of the keratin material a composition as defined in claim 1.

19. Cosmetic process for treating human perspiration and/or perspiration-related body odour, which comprises applying to the surface of a human keratin material a composition as defined in claim 17.

20. Composition according to claim 2, wherein the nonionic surfactant with a hydrocarbon-based chain comprising at least 16 carbon atoms is an alkylpolyglycoside.

21. Composition according to claim 1, having a hardness measured at 32° C. and at a humidity of 40% ranging from 25 kPa to 150 kPa.

* * * * *